(12) United States Patent
Choy et al.

(10) Patent No.: US 11,813,610 B2
(45) Date of Patent: Nov. 14, 2023

(54) MICROFLUIDIC DEVICES (71) Applicant: Hewlett-Packard Development Company, L.P., Spring, TX (US)

(72) Inventors: Silam J. Choy, Corvallis, OR (US); Hilary Ely, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 308 days.

(21) Appl. No.: 17/049,987

(22) PCT Filed: May 15, 2019

(86) PCT No.: PCT/US2019/032436
§ 371 (c)(1),
(2) Date: Oct. 23, 2020

(87) PCT Pub. No.: WO2020/013915
PCT Pub. Date: Jan. 16, 2020

(65) Prior Publication Data
US 2021/0229094 A1 Jul. 29, 2021

Related U.S. Application Data (63) Continuation of application No. PCT/US2018/041216, filed on Jul. 9, 2018.

(51) Int. Cl.
*B01L 3/00* (2006.01)
*G01N 33/487* (2006.01)

(52) U.S. Cl.
CPC ..... *B01L 3/502715* (2013.01); *B01L 3/50273* (2013.01); *B01L 3/502746* (2013.01);
(Continued)

(58) Field of Classification Search
CPC .......... B01L 3/502715; B01L 3/50273; B01L 3/502746; B01L 2200/12; B01L 2300/041;
(Continued)

(56) References Cited

U.S. PATENT DOCUMENTS 6,632,655 B1 10/2003 Mehta et al.
7,312,611 B1 12/2007 Harrison et al.
(Continued)

FOREIGN PATENT DOCUMENTS

KR 101388155 4/2014
WO 9909042 2/1999
(Continued)

OTHER PUBLICATIONS

Philippova, Olga, "Magnetic Polymer Beads: Recent trends and developments in synthetic design and applications", Jan. 8, 2011. European Polymer Journal, 47, pp. 542-559 (Year: 2011).*
(Continued)

*Primary Examiner* — Jill A Warden
*Assistant Examiner* — Alex Ramirez
(74) *Attorney, Agent, or Firm* — Foley & Lardner LLP (57) ABSTRACT

A microfluidic device includes a microfluidic chamber fluidly coupled to an inlet port and an outlet port, a semiconductor microchip including fluid active circuitry and transistor circuitry, and a bed of solid supports positioned within the microfluidic chamber fluidly positioned between the inlet port and the outlet port. The transistor circuitry in this example provides onboard logic at the semiconductor microchip to control fluid active circuitry. The semiconductor microchip also defines a portion of the microfluidic chamber.

20 Claims, 4 Drawing Sheets

(52) U.S. Cl.
CPC .... *G01N 33/48707* (2013.01); *B01L 2200/12* (2013.01); *B01L 2300/041* (2013.01); *B01L 2300/0663* (2013.01); *B01L 2400/043* (2013.01); *B01L 2400/0415* (2013.01); *B01L 2400/0421* (2013.01)

(58) Field of Classification Search
CPC ..... B01L 2300/0663; B01L 2400/0415; B01L 2400/0421; B01L 2400/043; G01N 33/48707
See application file for complete search history.

(56) References Cited

U.S. PATENT DOCUMENTS

| | | | |
|---|---|---|---|
| RE43,122 E * | 1/2012 | Harrison | B01L 3/5027 |
| | | | 204/453 |
| 8,551,714 B2 | 10/2013 | Jovanovich et al. | |
| 9,050,594 B2 | 6/2015 | Williams et al. | |
| 2003/0021734 A1 | 1/2003 | Vann et al. | |
| 2003/0077842 A1 | 4/2003 | Malmqvist et al. | |
| 2003/0215882 A1 | 11/2003 | Grossman et al. | |
| 2004/0245102 A1 | 12/2004 | Gilbert et al. | |
| 2006/0020371 A1 * | 1/2006 | Ham | G01R 33/3415 |
| | | | 700/266 |
| 2006/0051250 A1 | 3/2006 | Gonzalez et al. | |
| 2008/0160634 A1 | 7/2008 | Su et al. | |
| 2008/0259125 A1 | 10/2008 | Haluzak et al. | |
| 2009/0084679 A1 | 4/2009 | Harrison et al. | |
| 2010/0006439 A1 | 1/2010 | Ham et al. | |
| 2010/0165784 A1 | 7/2010 | Jovanovich et al. | |
| 2010/0255556 A1 | 10/2010 | Hunt et al. | |
| 2011/0206576 A1 * | 8/2011 | Woudenberg | B01F 33/30 |
| | | | 506/37 |
| 2013/0264205 A1 * | 10/2013 | Hwang | G01N 1/286 |
| | | | 204/601 |
| 2015/0174574 A1 | 6/2015 | Chang et al. | |
| 2017/0074758 A1 | 3/2017 | Motadel | |
| 2017/0341076 A1 * | 11/2017 | Yu | G01N 35/00871 |
| 2017/0350882 A1 | 12/2017 | Lin et al. | |
| 2018/0095067 A1 * | 4/2018 | Huff | G01N 33/48721 |
| 2018/0214878 A1 | 8/2018 | Chang et al. | |
| 2018/0257075 A1 | 9/2018 | Yellen et al. | |

FOREIGN PATENT DOCUMENTS

| | | | |
|---|---|---|---|
| WO | WO-9909042 A2 * | 2/1999 | ............. B01D 15/00 |
| WO | 0185341 | 11/2001 | |
| WO | 2013126774 | 8/2013 | |
| WO | 2016175864 | 11/2016 | |
| WO | WO-2017096414 A1 * | 6/2017 | ......... B01D 11/0496 |

OTHER PUBLICATIONS

Ghallab et al., CMOS Based Lab-on-a-Chip: Applications, Challenges and Future Trends, IEEE Circuits and Systems Magazine, vol. 14, No. 2, May 20, 2014, pp. 27-47.

Hakho et al., IC/Microfluidic Hybrid System for Magnetic Manipulation of Biological Cells, IEEE Journal of Solid Sate Circuits, vol. 41, No. 6, Jun. 2006, pp. 1471-1480.

International Search Report dated Aug. 22, 2019 for PCT/US2019/032436, Applicant Hewlett-Packard Development Company, L.P.

* cited by examiner

FIG. 10

MICROFLUIDIC DEVICES

BACKGROUND

Microfluidic devices can exploit chemical and physical properties of fluids on a microscale. These devices can be used for research, medical, and forensic applications, to name a few, to evaluate or analyze fluids using very small quantities of sample and/or reagent to interact with the sample than would otherwise be used with full-scale analysis devices or systems.

DETAILED DESCRIPTION

With microfluidics, the isolation or concentrating of target substances that may be dissolved or dispersed in a fluid can provide benefits with respect to subsequent processing, including measurement, chemical reaction or interaction, physical manipulation, or the like. Once isolated or concentrated, these or other subsequent processes can occur in situ within the microfluidics of a semiconductor microchip, for example. To illustrate, measurements can be performed using sensors on the semiconductor microchips, chemical reactions or interactions can be initiated within reaction chambers or microchannels, local heating can be carried out, physical fluidic or target substance manipulation can occur using MEMS components, etc. In further detail, a bed of solid supports, such as silica, ceramic, polymer, paramagnetic material, etc., in the form of beads, particles, fibers, or the like, can be used in conjunction with a semiconductor microchip, both of which would be in fluid communication with a fluid that may be introduced or passed through a microfluidic chamber. Thus, both the bed of solid supports and the fluid active circuitry can interact with the fluid within the chamber to process the fluid as may be useful for a particular application. For example, surfaces of the solid supports can be selected or even surface-modified to have a surface chemistry capable of selectively capturing a target substance from a fluid, such as a biological fluid. Target substances may include, for example, biological cells, proteins, nucleic acids, exosomes, and other compounds or particles. In further detail, the solid supports can be manufactured to be held within a chamber in preparation for a fluid to be introduced therein, where the fluid would interact with the bed of solid supports and also interact with the fluid active circuitry that is present within the microfluidic chamber. In some examples, unwanted components (other than the target substance) could be purged from the microfluidic chamber without much loss of the target substance, e.g., the target substance can become more concentrated.

In accordance with this example and others, the present disclosure is drawn to a microfluidic device including a microfluidic chamber fluidly coupled to an inlet port and an outlet port, a semiconductor microchip including fluid active circuitry and transistor circuitry, and a bed of solid supports positioned within the microfluidic chamber fluidly positioned between the inlet port and the outlet port. The transistor circuitry in this example provides onboard logic at the semiconductor microchip to control the fluid active circuitry. The semiconductor microchip also defines a portion of the microfluidic chamber. In one example, the microfluidic chamber can be further defined by a lid including a material selected from glass, quartz, polymer, amorphous polymer, or a combination thereof. In another example, the microfluidic chamber can likewise be defined by a support substrate that supports the semiconductor microchip, wherein the lid is sealed against the support substrate and the semiconductor microchip. The bed of solid supports can include, for example, silica, ceramic, polymer, or a combination thereof in the form of particles or fibers. The bed of solid supports can alternatively be paramagnetic particles. The bed of solid supports can further be surface-modified solid supports. In more specific examples, the semiconductor microchip can have an elongated aspect ratio with a width from 50 µm to 1 mm, a thickness from 50 µm to 1 mm, and a length of 1.5 mm to 50 mm. In this configuration, the inlet port and the outlet port can be positioned so that a flow of fluid therebetween is along the length of the semiconductor microchip. In other examples, the microfluidic chamber can have a volume from 1 nL to 100 µL. In further detail, the fluid active circuitry may include a heater, a sensor, an electromagnetic radiation source, a fluid actuator, or a combination thereof.

In another example, a method of making a microfluidic device includes forming a microfluidic chamber fluidly coupled to an inlet port and an outlet port, and disposing a bed of solid supports within the microfluidic chamber at a location fluidly positioned between the inlet port and the outlet port. In further detail, the microfluidic chamber is partially defined by a semiconductor microchip that includes fluid active circuitry and transistor circuitry to provide onboard logic at the semiconductor microchip to operate the fluid active circuitry. In one example, the microfluidic channel can also be partially defined by a lid, and disposing the bed of solid supports within the microfluidic chamber includes disposing the bed of solid supports within an area or microfluidic chamber formation, and then enclosing the area with the lid to form the microfluidic chamber with the bed of solid supports disposed therein. In another example, disposing the bed of solid supports within the microfluidic chamber can include flowing solid supports into the microfluidic chamber through one or both of the inlet port or the outlet port.

In another example, a method of electronically interacting with a target substance of a fluid includes flowing a fluid that includes a target substance through a bed of solid supports contained within a microfluidic chamber, and selectively retaining the target substance at the bed of solid supports while allowing secondary fluid components to exit the microfluidic chamber. The microfluidic chamber in this example is partially defined by a semiconductor microchip that includes transistor circuitry and fluid actionable circuitry. In further detail, the method includes electronically inducing an interaction between the target substance and the semiconductor microchip using the transistor circuitry to provide onboard logic to operate the fluid active circuitry. In one example, the target substance can be a nucleic acid, and the secondary fluid components include lysed cellular debris, among other examples. The onboard logic can, for example, control multiple operations of the fluid active circuitry based on conditions within the microfluidic chamber by selecting operations from multiple alternatives.

In addition to the examples described above, the microfluidic device, the method of manufacturing the microfluidic device, and the method of electronically interacting with a target substance of a fluid are described in greater detail below. It is also noted that when discussing the microfluidic device or one or both methods, such discussions of one example are to be considered applicable to the other examples, whether or not they are explicitly discussed in the context of that example. Thus, in discussing solids supports in the context of the microfluidic device, such disclosure is also relevant to and directly supported in the context of the methods, and vice versa.

Turning now to the FIGS. for further detail, as an initial matter, there are several components of the microfluidic devices shown that are common to multiple examples, and thus, the common reference numerals are used to describe various features. Thus, a general description of a feature in the context of a specific FIG. can be relevant to the other example FIGS. shown, and as a result, individual components need not be described and then re-described in context of another FIG. Thus, FIGS. 1-8 can be considered simultaneously in the description of the FIGS. to the extent relevant by a common reference numeral, for example.

In further detail, the representations of the microfluidic devices in the figures are merely intended to facilitate the description and presentation of the microfluidic devices disclosed herein. It is noted, however, that when discussing microfluidic devices, methods, or the like, such description is also intended to encompass mesofluidic devices. Thus, in some examples, the microfluidic chambers described herein can include sub-millimeter dimensions. In other examples, the microfluidic chambers can include from millimeter to centimeter dimensions. Thus, for simplicity, both microfluidics and mesofluidics are referred to herein as microfluidics, meaning generally what is being referred to are fluidics that use small quantities of fluids in the chambers, e.g., 1 nL to 100 µL, from 100 nL to 1 µL, from 1 µL to about 10 µL, or from 500 nL to 6 µL.

Figure 1:
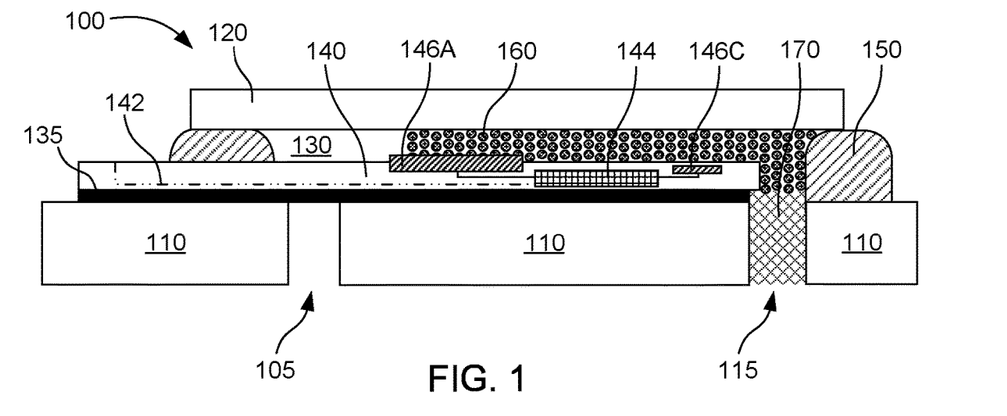
FIG. 1 graphically illustrates a schematic cross-sectional view of an example microfluidic device in accordance with the present disclosure.

With more specific reference to FIG. 1 (and other FIGS. with common features), a schematic cross-sectional view of an example microfluidic device 100 in accordance with the present disclosure is shown. As shown, the microfluidic device includes a support substrate 110 with an inlet port 105 and an outlet port 115. The inlet port and the outlet port can be used to provide fluid to (via the inlet port) and pass fluid from (via the outlet port) a microfluidic chamber 130. It is noted that the terms "inlet" and "outlet" do not infer that these ports interact with the microfluidic chamber in one direction, though that could be the case. In some instances, there may be occasion for the fluid to flow "backwards" or "bidirectionally," and thus the terms "inlet port" and "outlet port" are used because at some point during operation, these two ports act as inflow of fluid and outflow of fluid, respectively, relative to the microfluidic chamber.

In further detail, the microfluidic device 100 includes a semiconductor microchip 140 with transistor circuitry 144 that can use onboard logic to control fluid active circuitry 146A-146C, which can be in the form of any of a number of fluid active circuitry devices, such as fluid active circuit devices that operate as a heater (e.g., rapid thermal cycling heater, resistive heater, etc.), a sensor (e.g., photo sensor, thermal sensor, fluid flow sensor, chemical sensor, etc.), an electromagnetic radiation source (photo diode, laser, etc.), a fluid actuator (e.g., mixers, bubblers, pumps, etc.), or the like. A semiconductor microchip can operate with fewer electrical connections then other types of circuitry systems, and thus, a single or few data lines 142 may be used to operate multiple circuitry components, rather than having a separate conductive pad(s) and control trace for every fluid active circuit that may be present. In other words, with onboard logic provided by the transistor circuitry, there can be a reduced number of I/O ports present. This is because the operation can be controlled partially or fully by the transistor circuitry operating as a logic control for the fluid active circuitry. The transistor circuitry 144 may include an integrated circuit to perform the operations according to logical relationships or state transitions implemented in the transistor circuitry 144. The transistor circuitry 144 may include an application specific integrated circuit (ASIC), a Field Programmable Gate Array (FPGA), or the like.

In addition to the transistor circuitry 144, as mentioned, the semiconductor microchip 140 includes fluid active circuitry 146A-146C. In the various examples shown herein, there are multiple fluid active circuitry components shown in the various FIGS., but there could be fewer or more and/or there could be arrays of fluid active circuitry, etc. For example, there can be a single fluid active circuit, an array or one type of fluid active circuit, multiple types of fluid active circuits, arrays of multiple types of fluid active circuits, or any combination thereof. Particularly when there are multiple fluid active circuits present (by type, by array, and/or a single type), or when there are decisions to be made in the operation of the fluid active circuitry that would benefit from speed or efficiency, the use of an onboard transistor to provide logic control to the fluid active circuitry can be beneficial. For example, if an operation would benefit from maintaining a fluid within a narrow temperature range, a heater circuit or cooling functions can be used to keep the temperature with that narrow temperature range, e.g., within 1° C., within 0.5° C., or within 0.1° C., without sending signals on and off the semiconductor microchip to receive "decisions" from a CPU that is not part of the semiconductor microchip. Thus, by increasing response time to adjust temperature using onboard logic, the temperature may be able to be kept within a narrower target temperature range.

In some examples, the fluid active circuitry 146A-146C can be in physical contact with a fluid when fluid is introduced into the microfluidic chamber, or there may be a thin protective film or layer of material that protects the circuitry, but which does not interfere the function of the active circuitry in interacting with a fluid or target substance of a fluid. For example, there may be a protective film(s) or layer(s) of polymer, oxide, carbide, metal or alloy, nitride, silicon, etc. The thickness of a protective film(s) or layer(s) that may be included may range from the thickness of 0.3 nm (a single atom layer) to 50 μm, from 1 nm to 50 μm, from 10 nm to 40 μm, from 10 nm to 30 μm, from 10 nm to 1 μm, from 50 nm to 50 μm, from 50 nm to 30 μm, from 100 nm to 50 μm, from 500 nm to 50 μm, from 1 μm to 50 μm, from 5 μm to 50 μm, from 10 μm to 50 μm, from 1 μm to 30 μm, from 1 μm to 10 μm, from 1 nm to 500 nm, or from 1 nm to 200 nm, for example. These thicknesses tend to be thin enough that the fluid active circuitry can interact with the fluid or the target substance therein.

In further detail, the fluid active circuitry 146A-146C (coated or uncoated) can protrude into the microfluidic chamber (as shown at 146A), can be positioned along a surface that defines the microfluidic chamber (as shown at 146B), or can be beneath a surface of the semiconductor microchip (as shown at 146C), for example, or can be positioned just below a surface of the semiconductor microchip. As shown in this particular example, a portion of the semiconductor microchip is attached to the support substrate via an adhesive 135, for example, but could be attached, suspended, cantilevered, or included therein in any of a number of other ways.

As shown by way of example, the microfluidic chamber 130 contains a bed of solid supports 160, which can be any solid support structure that can be contained within the microfluidic chamber, but does not include solid supports that would otherwise be attached to a surface defining the microfluidic chamber. For example, a solid support would not include, pillars, wall protrusions, surface bumps or processes, surface cavities, or the like, attached to a surface of the microfluidic chamber. Rather, a "solid support" is defined herein to be a bead, particle, or fiber-like structure that is loaded as a separate structure within the microfluidic chamber. The solid supports can be added in a quantity to form a bed of solid supports within the microfluidic chamber. The volume occupied by the solid supports in the microfluidic chamber can be from 0.01 vol % to 99 vol %, from 0.1 vol % to 99 vol %, from 0.5 vol % to 99 vol %, from 1 vol % to 99 vol %, from 5 vol % to 99 vol %, from 1 vol % to 50 vol %, from 1 vol % to 25 vol %, from 1 vol % to 10 vol %, or from 1 vol % to 5 vol %, or from 5 vol % to 50 vol %, for example. Materials for use as solid supports include silica, ceramic, polymer, or a combination thereof. In another example, the solid supports can include paramagnetic particles (shown in FIGS. 7 and 8 at 165). Paramagnetic particles include any particle that interacts with a magnetic field 185, but when a magnetic field is not applied, the particles are not magnetically attracted to one another. Example paramagnetic particles include nano-sized ferrite material that is embedded or coated with a polymer. Other examples may include Dynabeads®, MyOne™ Silane, or DNA Direct Universal (ThermoFisher Scientific, USA), such as Dynabeads® or others with various modified surface chemistry. Another example is MagaZorb® beads (Promega Life Sciences, USA).

Example surface modifications for the various types of solid supports described herein, including both nonmagnetic supports and paramagnetic supports include antibodies, streptavidin, oligomers, e.g., sequence specific oligomers, functional groups including amines and/or carboxyl groups, or the like. Other surface modifications that can be used include modification with covalently attached ligands, such as with organosilanes or other linking groups having functional groups appended thereto, e.g., functional moieties selective for nucleic acids or even functional moieties selective of a specific base or nucleic acid sequence.

In further detail regarding the solid supports 160, the particles (or other shaped solid support material) can be selected based on the specific application. For example, if loading solid supports into a microfluidic chamber 130 where a filter 170 is used to retain the particles within the microfluidic chamber, then the average particle size can be from 250 nm to 100 μm, from 500 nm to 10 μm, from 1 μm to 10 μm, from 500 nm to 5 μm, or from 750 nm to 8 μm and may have acceptable utility. If the solid supports are elongated, such as fibers, then then the aspect ratio can be from about 1:2 width to length) to about 1:200, for example, with a cross-sectional average diameter size ranging from 20 nm to 10 μm, for example. When selecting or designing a filter for use, a balance of effective pore size to retain solid supports within the microfluidic chamber with fluid penetration through the microfluidic chamber and out of the outlet port 115 can be considered, e.g., considering filtration efficiency vs. flow resistance. If, for example, the solid supports are from 250 nm to 100 μm in size, for filtration, the effective pore size can be up to about 75% of the average size of the solid supports to retain most of the solid support material. Pore size is difficult to quantify based on opening size, as there are 2D and 3D meshes, screens, networks of pillars or columns, pores, foams, air bubbles, fibrous structures, etc., of many different configurations, but in terms of operation in the microfluidic devices of the present disclosure, a filter can be used with solid support material that has a filtration efficiency that retains 99% (or more) of the D10 particles (or fibers) of the bed of solid supports. The filter can be a mesh or screen, pillars and columns in the chamber, pores in polymer foam, pores in fibrous structures, etc.

On the other hand, if loading paramagnetic solid supports (shown at 165 at FIG. 7 and FIG. 8), then instead of filtration (or in addition to filtration), a magnetic field can be used to retain the solid supports. With paramagnetic particles, smaller particles can be used as there is less concern with flow resistance that can be introduced by the use of a filter. Thus, the average particle sizes can be inclusive of smaller particles, e.g., from 20 nm to 100 μm, from 20 nm to 10 μm, from 50 nm to 5 μm, from 100 nm to 3 μm, or from 200 nm to 2 μm. A magnetic field 185 passing into the fluid volume can be provided by a nearby magnet 180, which can be a permanent magnet or electromagnet that has enough strength to capture paramagnetic microbeads inside the chamber as fluid flows through the solid supports within the microfluidic chamber. Thus, unwanted components that do not interact with the solid supports can be freely purged from the microfluidic chamber via the outlet port 115, for example, without the loss of the paramagnetic solid supports (and the target substance associated with a surface thereof). In this example, the magnetic field can be strong enough to continue to hold the paramagnetic solid supports as any additional fluid is pumped through the microfluidic chamber. In further detail, the magnetic field properties can be modifiable by translating or rotating one or more magnets, or by introducing and or turning off (or modulating) the electric current through an electromagnet. Magnet(s) of any type may be placed above, below, or beside the microfluidic chamber. Polar orientation can also be determined based on magnetic field properties that may be useful in acting appropriately on the paramagnetic solid supports.

The term "particle size" is used synonymously with "D50 particle size" when referring to a group or distribution of particles, e.g., such as a bed of solid supports. The D50 particle size is defined as the particle size at which about half of the particles are larger than the D50 particle size and about half of the other particles are smaller than the D50 particle size by weight. Furthermore, particle size refers to the value of the diameter of spherical particles, or when particles are not spherical, refers to particle size of the volume of the particles with the particle volume normalized to a spherical shape.

In further detail regarding FIG. 1, the microfluidic chamber 130 can be defined on multiple sides by multiple structures. For example, the microfluidic chamber as shown in FIG. 1 can be defined by a portion of a surface of the semiconductor microchip 140, including fluid active circuitry 146A, 146B, 146C thereof. A lid 120 and a seal 150 also further define the microfluidic chamber. Though not visible from the view shown in FIG. 1, FIGS. 2A (or 2B) and 3 show that the support substrate 110 also contributes to defining the microfluidic chamber.

A variety of suitable support substrates 110 can be used. Typically, any support substrate to which a semiconductor microchip 140 (or a semiconductor microchip and a lid 120 in some examples) can be mounted, and that is suitable for a particular application, can be used. In some specific examples, the support substrate can include or be made of a material such as metal, glass, silicon, silicon dioxide, a ceramic material (e.g., alumina, aluminum borosilicate, etc.), a polymer material (e.g., polyethylene, polypropylene, polycarbonate, poly(methyl methacrylate), epoxy molding compound, polyamide, liquid crystal polymer (LCP), polyphenylene sulfide, etc.), the like, or a combination thereof. Additionally, the support substrate can have any suitable dimensions for a given application. In some examples, the support substrate and the lid can be architecturally compatible to form a complete seal at their interface. In other examples, the support substrate and the lid can be architecturally compatible so that a seal 150, such as a sealing adhesive, can be positioned between the support substrate and the lid to form or enclose the microfluidic chamber 130. Other arrangements that also use a support substrate can likewise be used, such as support substrates that support a cantilevered or suspended (bridge-like) semiconductor microchip within the microfluidic chamber, as shown by example in FIG. 5. In that example, the support substrate supports the semiconductor microchip just outside of the microfluidic chamber at one end using an adhesive 135, and the support substrate supports the semiconductor microchip at another end within the microfluidic chamber also using an adhesive, thereby forming a bridged semiconductor microchip with microfluidic chamber with space both above and below the semiconductor microchip. In this arrangement, there may be fluid active circuitry (not shown in FIG. 5 but shown by example in FIG. 1) on both sides of the semiconductor microchip.

The semiconductor microchip 140 can be any configuration that is suitable for performing a function as described herein. The semiconductor microchip can be a CMOS semiconductor microchip, for example. In addition to silicon-based semiconductor chips, other examples can include gallium arsenide or gallium nitride semiconductor chips. In one example, the semiconductor microchip can be an elongated semiconductor microchip. By "elongated semiconductor microchip," it is to be understood that the semiconductor microchip can have a width to length where the width is narrower than the length. Example aspect ratios include width to length ratios such as 1:10 to 1:200, from 1:10 to 1:150, 1:10 to 1:100, from 1:10 to 1:50, or from 1:20 to 1:00, for example. There is also a thickness component to the ratio. Thickness for the semiconductor microchip can vary but can be thin enough to leave space in the microfluidic chamber to allow for fluid flow through the bed of solid supports for fluid interaction with the fluid active circuitry.

Figure 5:
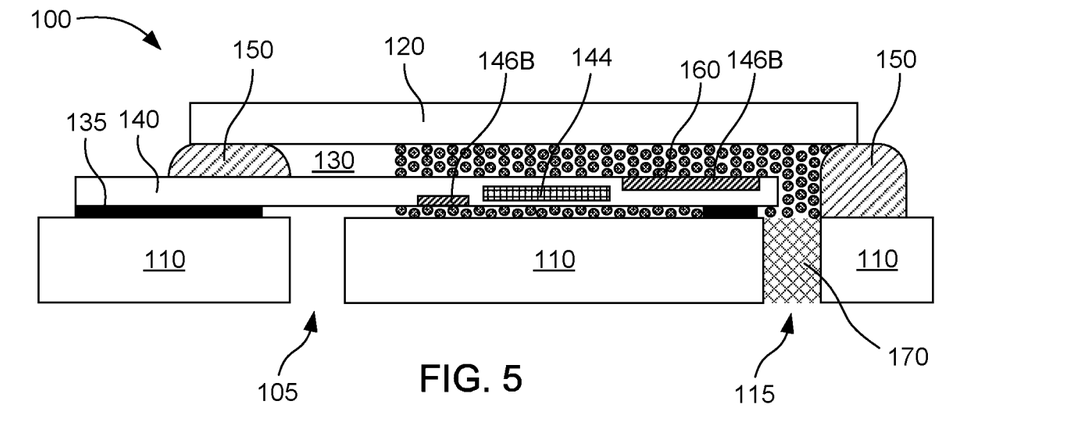
FIG. 5 graphically illustrates a schematic cross-sectional view of an example microfluidic device in accordance with the present disclosure.
Figure 8:
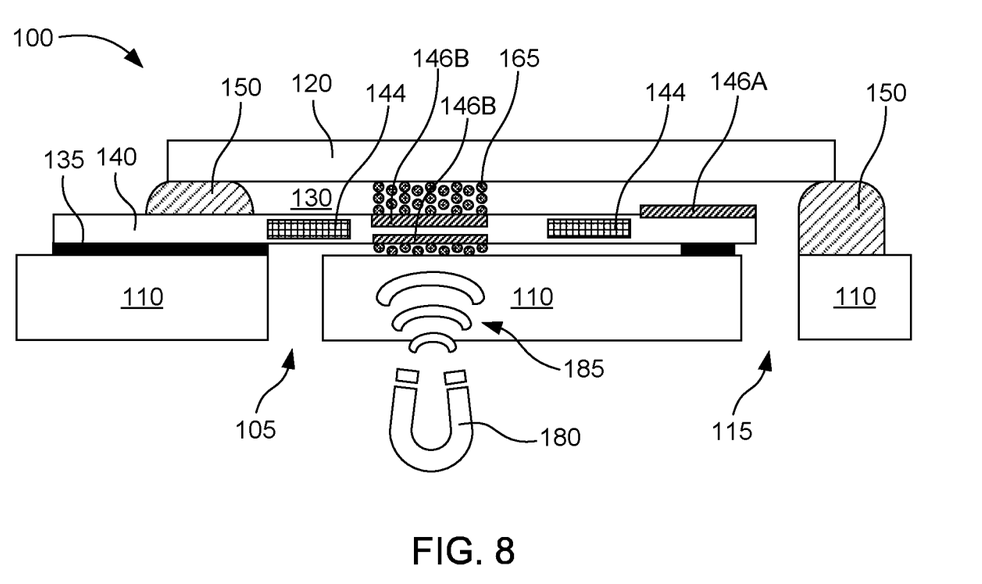
FIG. 8 graphically illustrates a schematic cross-sectional view of an example microfluidic device in accordance with the present disclosure.

In examples herein, a top surface (or portion thereof) defined by the length and width can be in contact with fluid within the microfluidic chamber, but in some examples, there can also be sides of the semiconductor microchip or a bottom surface of the semiconductor microchip that can be in contact with the fluid as well (see FIGS. 5 and 8, for example). It is noted that in referring to a structure using a term such as "top," "side," or "bottom," these are considered to be relative terms that do not infer orientation, as the devices can be used in any orientation. Thus, the term "top" for example, is a term indicating location or a surface relative to a support substrate structure to which the semiconductor chip is supported in several of the example FIGS. As another example, if positioned vertically, the support substrate and another structure, such as a lid, would be positioned side by side. But the lid is shown in the FIGS. as being on "top" of the support substrate. Thus, in this context, as orientation is not inferred, the term "top" and other terms should be considered to be relative terms in the context of the FIGS.

The length of the semiconductor microchip can be, for example, from 1.5 mm to 50 mm, from 5 mm to 50 mm, from 10 mm to 40 mm, from 10 mm to 30 mm, from 15 mm to 50 mm, from 20 mm to 50 mm, or from 15 mm to 40 mm, for example. The width of the semiconductor microchip can be, for example, from 50 µm to 1 mm, from 100 µm to 1 mm, from 200 µm to 1 mm, from 500 µm to 1 mm, from 200 µm to 800 µm, or from 300 µm to 700 µm, for example. The thickness of the semiconductor microchip can be, for example, from 50 µm to 1 mm, from 100 µm to 1 mm, from 200 µm to 1 mm, from 500 µm to 1 mm, from 200 µm to 800 µm, or from 300 µm to 700 µm, for example.

In other examples, wherein the semiconductor microchip is not an elongated semiconductor microchip, the shape of the semiconductor microchip can be rectangular (including square), elliptical, circular, arcuate, polygonal, trapezoidal, or any other geometric shape. In further detail, the semiconductor microchip can be made of a variety of support materials, such as silicon, glass, quartz, ceramic, or the like. The fluid active circuitry can be in electrical communication with circuitry or other components outside of the microfluidic chamber via a wire, a trace, a network of wires, a network of traces, an electrode, a conductive pad, and/or any other electrical communication structure that may or may not be embedded in the semiconductor microchip support material. The fluid active circuitry that is included as part of the semiconductor microchip and which is in fluid communication with the microfluidic chamber (to interact in contact with fluid or interact with fluid beneath a thin film(s) or layer(s) on the semiconductor microchip) can be in the form of any of a number of fluid active circuitry components, including heaters, sensors, electromagnetic radiation sources, fluid actuators (e.g., mixers, bubblers, fluid pumps, etc.). In some examples, there can be multiple different types of fluid active circuitry components, e.g. a heater for rapid thermal cycling and a sensor to confirm something occurring within the microfluidic chamber. For example, a heater can be used for rapid thermal cycling to amplify DNA, and a sensor can be present to confirm the temperature profile and/or the presence of amplified DNA. Other combinations can be designed to work for a variety of specific purposes. Regardless, the fluid active circuitry described herein includes circuitry that is positioned to interact with the fluid(s) which flow into or through the microfluidic chamber, either with direct contact or protected by a thin film(s) or layer(s) of protective material, depending on the active circuitry materials and function.

Figure 2A:
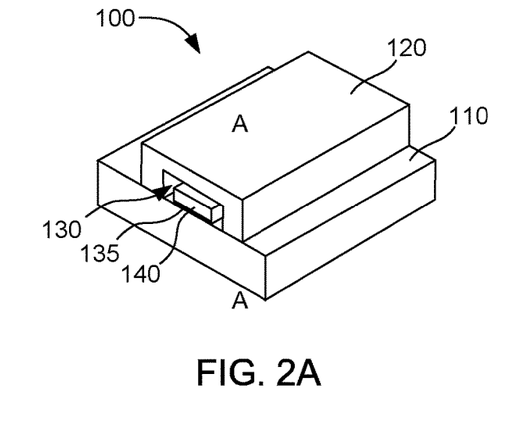
FIG. 2A graphically illustrates a schematic perspective view of a portion of a microfluidic device in accordance with the present disclosure.
Figure 2B:
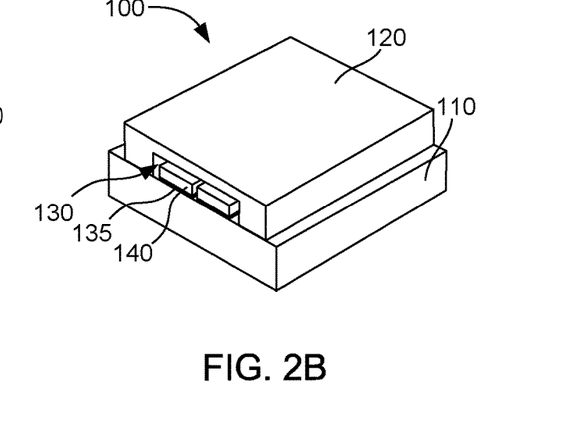
FIG. 2B graphically illustrates a schematic perspective view of a portion of alternative microfluidic device in accordance with the present disclosure.
Figure 3:
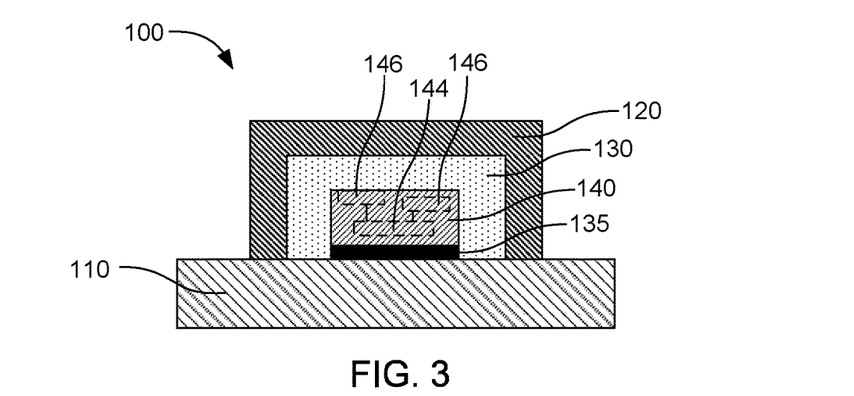
FIG. 3 graphically illustrates a schematic cross-sectional view of an example microfluidic device in accordance with the present disclosure.
Figure 4:
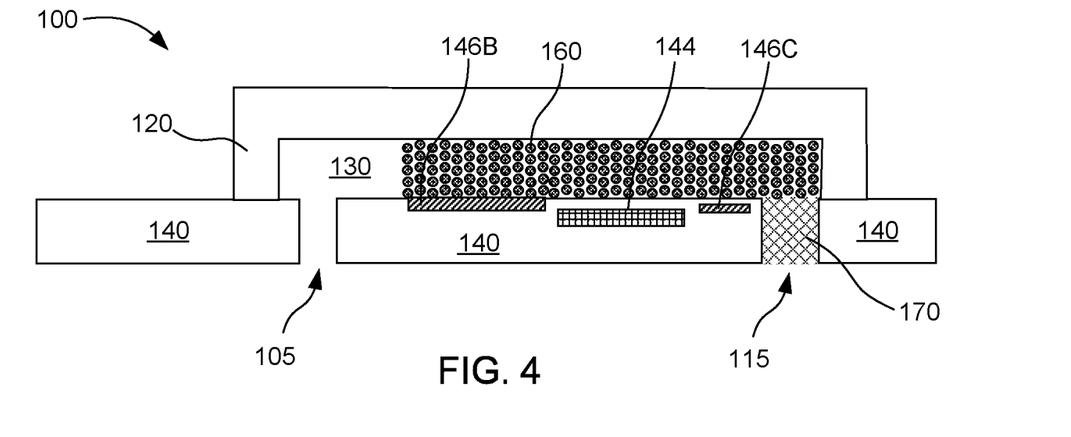
FIG. 4 graphically illustrates a schematic cross-sectional view of an example microfluidic device in accordance with the present disclosure.
Figure 6:
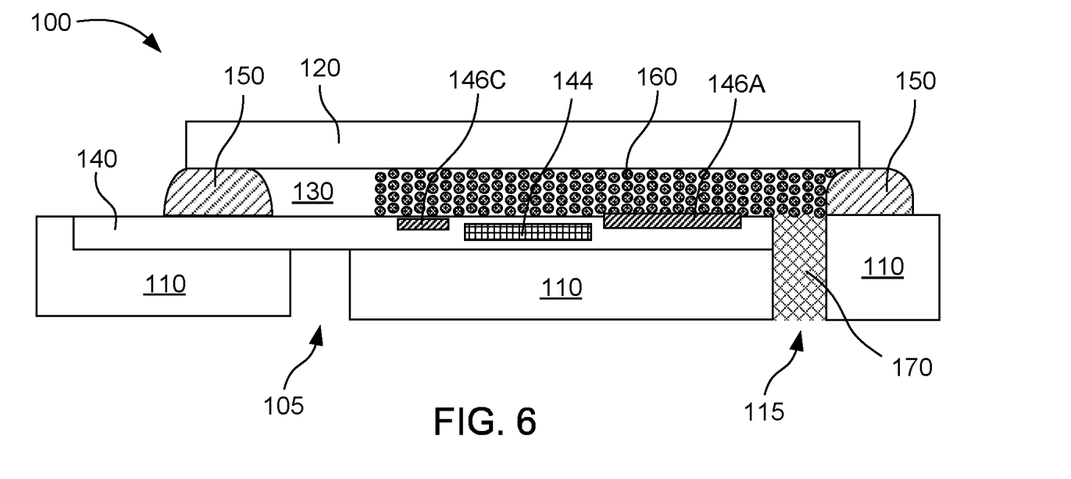
FIG. 6 graphically illustrates a schematic cross-sectional view of an example microfluidic device in accordance with the present disclosure.
Figure 7:
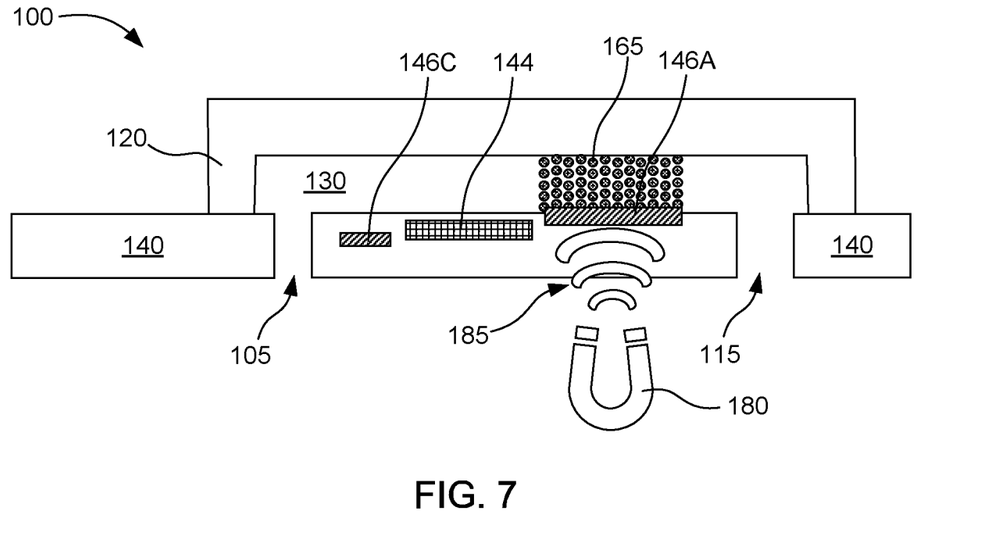
FIG. 7 graphically illustrates a schematic cross-sectional view of an example microfluidic device in accordance with the present disclosure.

Regarding the lid 120 (or cover), the lid can be any configuration that us usable for contributing to forming the microfluidic chamber. For example, the lid can have a "U-shape" as shown in FIG. 2A, FIG. 2B, and FIG. 3. Alternatively, the lid can have a flat shape, with walls provided by a separate wall structure. In either case, the lid can be fitted to attach to the support substrate 110, as shown in FIGS. 2A and 2B, to both the support substrate at some locations and to the semiconductor microchip 140 at other locations, as shown in FIGS. 1, 5, and 6, or to the semiconductor microchip, as shown in FIG. 4. Alternatively, the lid may have a more complicated shape or configuration, such as shaped to provide multiple discrete microfluidic chambers between semiconductor microchips, fluid active circuitry thereon, or other structures. In another example, the microfluidic device can include a second lid that can form a second discrete microfluidic chamber between semiconductor microchips or fluid active circuitry of semiconductor microchips. Furthermore, as shown in the example FIGS. herein, the various inlet ports 105 and the outlet ports 115 are shown as being provided by the support substrate and/or semiconductor microchip. However, it is understood that the inlet and/or outlet port can likewise be provided by the lid, for example. The positioning of the inlet port and/or outlet port is not particularly limited, except that the inlet port and the outlet port can be positioned so that fluid flow (at some point in time) flows through the bed of solid supports 160. In further detail, the lid may provide other ports, such as vents or other structures for facilitating fluid flow through the microfluidic chamber.

The lid can be prepared or selected from materials, such as glass, quartz, metal, polymer, e.g., amorphous polymer, or other suitable materials. Non-limiting examples of polymers can include polydimethylsiloxane (PDMS), cyclic olefin polymer (COP), cyclic olefin copolymer (COC), polyethylene terephthalate (PET), and/or the like. In some examples, the lid can include or be made of a transparent or translucent material such as glass, quartz, polycarbonate, Trivex™ (PPG Industries, USA), cyclic olefin copolymer (COC), and/or the like. In some examples, the lid can include or be made of a non-translucent material, such as silicon, a metal, and/or the like. In some examples, the material used to manufacture the lid can be doped with a dopant to enhance thermal performance, optical performance, chemical performance, and/or the like. Non-limiting examples of dopants can include erbium, $AlO_x$, $TaO_x$, etc. Composites of multiple materials can likewise be used to form the lid.

In some examples, with respect to the lid dimension, referring to the largest lid surface structure or lid "top," e.g., typically the lid surface opposite the support substrate, the structure of that portion of the lid can have dimensions that may be larger than the dimensions of a portion of the semiconductor microchip that is within the microfluidic chamber, for example, though this may not be the case in all instances.

Regarding the thickness of the lid 120 in particular, the thickness can vary depending on the particular application for which the microfluidic device 100 may be used. In some examples, the lid can have a thickness of from 0.1 mm to 10 mm, from 0.1 mm to 5 mm, from 0.2 mm to 2.5 mm, from 0.5 mm to 5 mm, or from 0.3 mm to 2 mm, for example. Thicknesses outside of this range can likewise be used, particularly if the thickness of the lid is not involved in a specific function that benefits from the lid thickness. For example, in some examples, the lid can be designed to be relatively thin to provide a function for a given application, such as to provide acceptable optical clarity (depending on the material, etc.), to provide acceptable heat dissipation from the microfluidic chamber 130, etc. Where a thinner lid is used, the lid can have a thickness of from 0.1 mm to 1 mm, or from 0.1 mm to 0.5 mm, for example. In other examples, a thicker lid may provide a desired property, such as decreased optical clarity or translucence, increased thermal insulation, etc. (as compared to a thinner lid). Where a thicker lid may be selected for use, the lid can generally have a thickness of from 0.5 mm to 10 mm, from 1 mm to 10 mm, or from 1 mm to 5 mm, for example. Further still, in some examples, it can be desirable to have a lid with a "non-uniform thickness" along one or more of the surfaces, e.g., the surface opposite the support substrate or top surface of the lid, as shown in FIG. 1 by example. A lid with a non-uniform thickness would include lids with thickness differentials that are not merely artifacts of manufacturing processes, but affirmatively designed lids with thickness differentials at various locations, e.g., two thicknesses at two locations that are coplanar (top portion of lid with two thicknesses), a sidewall thickness that is different than the top portion thickness, etc. This can be done for any of a number of reasons, such as to achieve structural, mechanical, functional, or other properties related to the lid structure. In further detail, the lid can be formed in a variety of ways, such as by injection molding, cast molding, compression molding, etching, cutting, melting, drilling, routing, and/or the like.

There are various structures that can be bonded or sealed together, and such bonding or formation of seals can be carried out using any of a number of technologies. To illustrate, in order to manufacture a microfluidic device 100, the semiconductor microchip 140 can be mounted on or supported by a support substrate 110. The lid 120 can also be mounted to the support substrate and/or the semiconductor microchip to form the microfluidic chamber 130 between the various structures. A seal 150 can be applied between structures to bond structures together around joints or can be applied to multiple structures to provide spacing between structures to contribute to providing the microfluidic chamber (See FIGS. 1, 5, 6, and 8). The semiconductor microchip can be bonded to the support substrate by an adhesive 135 or other bonding technology, as shown in FIGS. 1-3, 5, and 8. In other examples, the semiconductor microchip can be overmolded by the support substrate, as shown in FIG. 6. Other bonding techniques that can be used include wire bonding, die bonding, flip chip mounting, surface mount interconnect bonding, or the like. With respect to the use of adhesive between the support substrate and the semiconductor microchip, or between the lid and the support substrate and/or the semiconductor microchip, the adhesive can be a curable adhesive, such as an electromagnetic radiation curable adhesive, a heat curable adhesive, a chemical curable adhesive, or the like. In other examples, any of these structures can be fused together by welding, e.g., laser welding, ultrasonic welding, thermosonic welding, etc.

Figure 9:
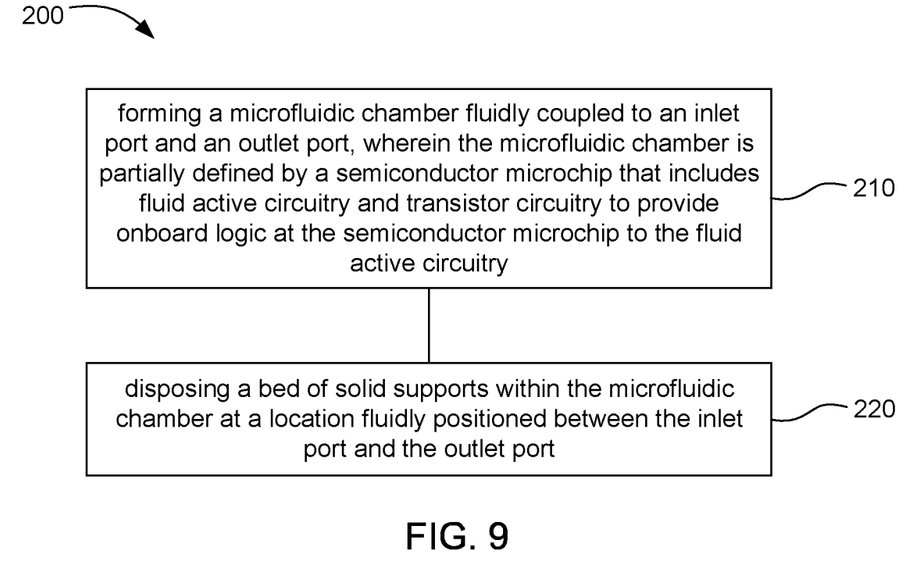
FIG. 9 is a flow diagram illustrating an example method of manufacturing a microfluidic device in accordance with the present disclosure.

In accordance with other examples, as shown in FIG. 9, a method 200 of making a microfluidic device includes forming 210 a microfluidic chamber fluidly coupled to an inlet port and an outlet port, and disposing 220 a bed of solid supports within the microfluidic chamber at a location fluidly positioned between the inlet port and the outlet port. In further detail, the microfluidic chamber is partially defined by a semiconductor microchip that includes fluid active circuitry and transistor circuitry to provide onboard logic at the semiconductor microchip to the fluid active circuitry. In one example, the microfluidic channel can also be partially defined by a lid, and disposing the bed of solid supports within the microfluidic chamber includes disposing the bed of solid supports within an area of microfluidic chamber formation, and then enclosing the area with the lid to form the microfluidic chamber with the bed of solid supports disposed therein. In another example, disposing the bed of solid supports within the microfluidic chamber can include flowing solid supports into the microfluidic chamber through one or both of the inlet ports or the outlet ports.

Figure 10:
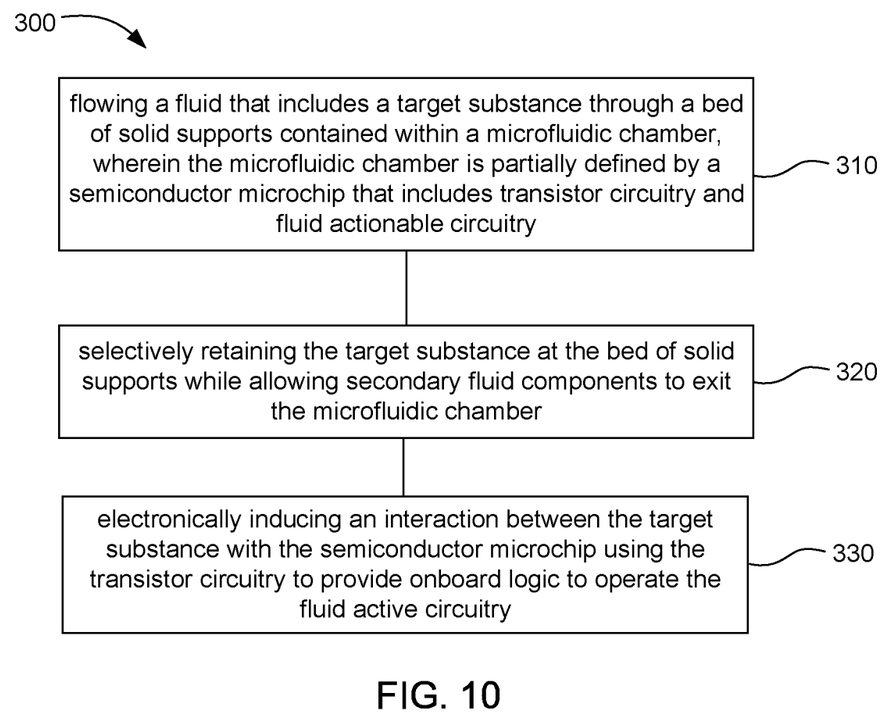
FIG. 10 is a flow diagram illustrating an example method of electronically interacting with a target substance of a fluid in accordance with the present disclosure.

In another example, as shown in FIG. 10, a method of electronically interacting with a target substance of a fluid includes flowing 310 a fluid that includes a target substance through a bed of solid supports contained within a microfluidic chamber, and selectively retaining 320 the target substance at the bed of solid supports while allowing secondary fluid components to exit the microfluidic chamber. The microfluidic chamber in this example is partially defined by a semiconductor microchip that includes transistor circuitry and fluid actionable circuitry. In further detail, the method includes electronically inducing 330 an interaction between the target substance and the semiconductor microchip using the transistor circuitry to provide onboard logic to operate the fluid active circuitry. In one example, the target substance can be a nucleic acid, and the secondary fluid components include lysed cellular debris, among other examples. The onboard logic can, for example, control multiple operations of the fluid active circuitry based on conditions within the microfluidic chamber by selecting operations from multiple alternatives.

In accordance with this and other methods, one potential application for which the microfluidic devices of the present disclosure can be useful is in the extraction of nucleic acids, and in some examples, further work can be done relative to these extracted nucleic acids, e.g., amplification, post amplification purification, e.g. PCR purification, fluid analysis, and/or downstream applications such as cellular transfection. For example, a nucleic acid or nucleic acid sequence can be attracted to surfaces of the solid supports, e.g., covalent attachment, electrostatic attraction, adsorption, etc., from one fluid feed, and then with the concentrated nucleic acids or nucleic acid sequences concentrated thereon, a different fluid could be flowed through that introduces another property, e.g., ionic strength, pH, concentrations, etc., to carry out the second action. Chaotropic and/or kosmotropic agents associated with the solid supports could be used to encourage the adsorption of the nucleic acids to a surface of the solid supports, for example. Wash buffers, in some examples, can be introduced to a bed of silica solid supports to provide a surface that becomes attractive to target substances that may be flowing or may be extractable from a specific fluid. Fluids could be introduced, such as master mixes, that could be used for nucleic acid amplification and heat provided by the fluid active circuitry, etc.

Another example application may be to establish paramagnetic solid supports in a bed at a location or at a packing density that is less restrictive or unrestrictive with respect to fluid flow, e.g., upstream from fluid flow, in a loose configuration, etc. A flow of fluid could then be introduced through the microfluidic chamber (from inlet port to outlet port), and then the paramagnetic beads reconfigured to enhance the flow restriction (create more flow resistance). For example, the bed of paramagnetic solid supports could be moved into the flow path or could be induced to be more tightly packed based on the introduction (or change) of a magnetic field relative to the paramagnetic solid supports.

In other examples, the fluid introduced into the microfluidic chamber can include lysed cells, which could be used for nucleic acids for amplification, antibody capture antibody, or the like. DNA or RNA could be purified, extracted, or otherwise separated from other cell components for amplification or for other purposes. For example, a sample that may include nucleic acids or proteins, such as from urine, blood, a swab, a plant sample, or the like, could be provided by lysing of cells, and then unwanted components or contaminants of the lysed cells could be cleared away, e.g., cell debris, blood cells (if not targeting blood samples), etc. Once the debris and other unwanted material has been passed downstream of the microfluidic chamber, an elution compound or buffer could be used to release the target component therefrom. In some instances, a wash buffer could be sent therethrough prior to the elution compound or buffer. Alternatively, it may be the target components of the fluid are not what is of interest, and they are captured so that they may be removed from the fluid, e.g., the solid supports may remove or be attracted to cell debris or unwanted chemical components, and the remaining fluid components could then be collected for use downstream from the microfluidic chamber. Either way, while in the microfluidic chamber, the fluid active circuitry of the semiconductor microchip may generate heat and provide sensor functions, e.g., electrochemical sensors, mixing, etc. For example, a sensor may be able to determine whether a sufficient amount of the debris and other chemical or biological components have been removed or are still present in preparation for carrying out the next function.

It is noted that, as used in this specification and the appended claims, the singular forms "a," "an," and "the" include plural referents unless the content clearly dictates otherwise.

As used herein, the term "about" is used to provide flexibility to a numerical range endpoint by providing that a given value may be "a little above" or "a little below" the endpoint. The degree of flexibility of this term can be dictated by the particular variable and can be determined based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

What is claimed is:

1. A microfluidic device, comprising:
   a microfluidic chamber fluidly coupled to an inlet port and an outlet port;
   a semiconductor microchip including fluid active circuitry and transistor circuitry, wherein the fluid active circuitry includes one or more of a heater, a sensor, an electromagnetic radiation source, or a fluid actuator, wherein the transistor circuitry provides onboard logic at the semiconductor microchip to control the fluid active circuitry, and wherein the semiconductor microchip defines a portion of the microfluidic chamber; and
   a bed of solid supports positioned within the microfluidic chamber fluidly positioned between the inlet port and the outlet port;
   wherein the microfluidic chamber is further defined by a lid including a material selected from glass, quartz, polymer, amorphous polymer, or a combination thereof, and
   wherein the microfluidic chamber is further defined by a support substrate that supports the semiconductor microchip, wherein the lid is sealed against the support substrate at a first seal, and the semiconductor microchip at a second seal.

2. The microfluidic device of claim 1, wherein the bed of solid supports includes silica, ceramic, polymer, or a combination thereof in the form of particles or fibers.

3. The microfluidic device of claim 1, wherein the bed of solid supports includes paramagnetic particles.

4. The microfluidic device of claim 1, wherein the bed of solid supports includes surface-modified solid supports.

5. The microfluidic device of claim 1, wherein the semiconductor microchip has an elongated aspect ratio with a width from 50 μm to 1 mm, a thickness from 50 μm to 1 mm, and a length of 1.5 mm to 50 mm, wherein the inlet port and the outlet port are positioned so that a flow of fluid therebetween is along the length of the semiconductor microchip.

6. The microfluidic device of claim 1, wherein the microfluidic chamber has a volume from 1 nL to 100 μL.

7. The microfluidic device of claim 1, wherein the transistor circuitry further provides the onboard logic at the semiconductor microchip to electronically induce an interaction between a target substance in the microfluidic chamber and the semiconductor microchip.

8. The microfluidic device of claim 1, wherein the bed of solid supports is in contact with the portion of the microfluidic chamber defined by the semiconductor microchip.

9. The microfluidic device of claim 1, wherein the bed of solid supports includes paramagnetic particles that are reconfigurable between a first position or density and a second position or density, the second position or density being more restrictive to fluid flow through the microfluidic chamber than the first position or density.

10. The microfluidic device of claim 1, wherein the fluid active circuitry includes a heater and a fluid actuator.

11. The microfluidic device of claim 1, wherein the lid forms the microfluidic chamber with the bed of solid supports disposed therein.

12. A microfluidic device, comprising:
    a microfluidic chamber fluidly coupled to an inlet port and an outlet port;
    a semiconductor microchip including first circuitry and second circuitry, wherein the first circuitry includes one or more of a heater, a sensor, an electromagnetic radiation source, or a fluid actuator, wherein the second circuitry provides onboard logic to control the first circuitry, and wherein the semiconductor microchip defines a portion of the microfluidic chamber; and
    a bed of solid supports positioned within the microfluidic chamber fluidly positioned between the inlet port and the outlet port;
    wherein the microfluidic chamber is further defined by a lid and a support substrate that supports the semiconductor microchip, wherein the lid is sealed against the support substrate at a first seal, and wherein the lid is sealed against the semiconductor microchip at a second seal.

13. The microfluidic device of claim 12, wherein the lid includes a material selected from glass, quartz, polymer, amorphous polymer, or a combination thereof.

14. The microfluidic device of claim 12, wherein the bed of solid supports includes silica, ceramic, polymer, or a combination thereof in the form of particles or fibers.

15. The microfluidic device of claim 12, wherein the bed of solid supports includes paramagnetic particles.

16. The microfluidic device of claim 12, wherein the bed of solid supports includes surface-modified solid supports.

17. The microfluidic device of claim 12, wherein the semiconductor microchip has an elongated aspect ratio with a width from 50 μm to 1 mm, a thickness from 50 μm to 1 mm, and a length of 1.5 mm to 50 mm, wherein the inlet port and the outlet port are positioned so that a flow of fluid therebetween is along the length of the semiconductor microchip.

18. The microfluidic device of claim 12, wherein the second circuitry further provides the onboard logic at the semiconductor microchip to electronically induce an interaction between a target substance in the microfluidic chamber and the semiconductor microchip.

19. The microfluidic device of claim 12, wherein the bed of solid supports is in contact with the portion of the microfluidic chamber defined by the semiconductor microchip.

20. The microfluidic device of claim 12, wherein the bed of solid supports includes paramagnetic particles that are reconfigurable between a first position or density and a second position or density, the second position or density being more restrictive to fluid flow through the microfluidic chamber than the first position or density.

* * * * *